United States Patent [19]

Wright

[11] Patent Number: 5,720,282

[45] Date of Patent: Feb. 24, 1998

[54] UNIVERSAL RESPIRATORY APPARATUS AND METHOD OF USING SAME

[76] Inventor: Clifford Wright, 12737 Isocome St., San Diego, Calif. 92129

[21] Appl. No.: 708,253

[22] Filed: Sep. 6, 1996

[51] Int. Cl.[6] .................. A61M 16/00; A61M 25/00
[52] U.S. Cl. .................. 128/207.14; 128/203.12; 128/207.16; 128/912; 128/719; 128/725
[58] Field of Search .................. 128/207.14, 207.16, 128/207.12, 910, 911, 912, 716, 719, 725, 203.12; 604/266, 267, 268, 283, 284

[56] References Cited

U.S. PATENT DOCUMENTS

| | | | |
|---|---|---|---|
| 4,723,543 | 2/1988 | Beran | 128/725 |
| 4,951,661 | 8/1990 | Sladek | 128/912 |
| 4,967,743 | 11/1990 | Lambert | 128/207.16 |
| 5,431,157 | 7/1995 | Mourkidou et al. | 128/203.12 |
| 5,449,348 | 9/1995 | Dryden | 128/207.16 |

*Primary Examiner*—Vincent Millin
*Assistant Examiner*—V. Srivastava
*Attorney, Agent, or Firm*—Jerry R. Potts

[57] ABSTRACT

A closed ventilator system includes a universal endotrachael tube adapter having a pair of interconnected hollow body members. One of the hollow body members includes a pair of interconnected air passageways coupled respectively between a ventilator and an endotrachael tube, where the air passageway coupled to the endotrachael tube includes a universal access port for receiving a measurement gauge or a suction catheter device. The other hollow body member is adapted to receive a valve which is maintained in a normally open position to permit air under pressure from the ventilator to be supplied to the endotrachael tube. However, when the measurement gauge or suction device is attached to the access port, the valve can be manually operated to close the passageway to the ventilator without closing the other air passageway to facilitate accurate breathing measurement or fluid removal procedures.

15 Claims, 5 Drawing Sheets

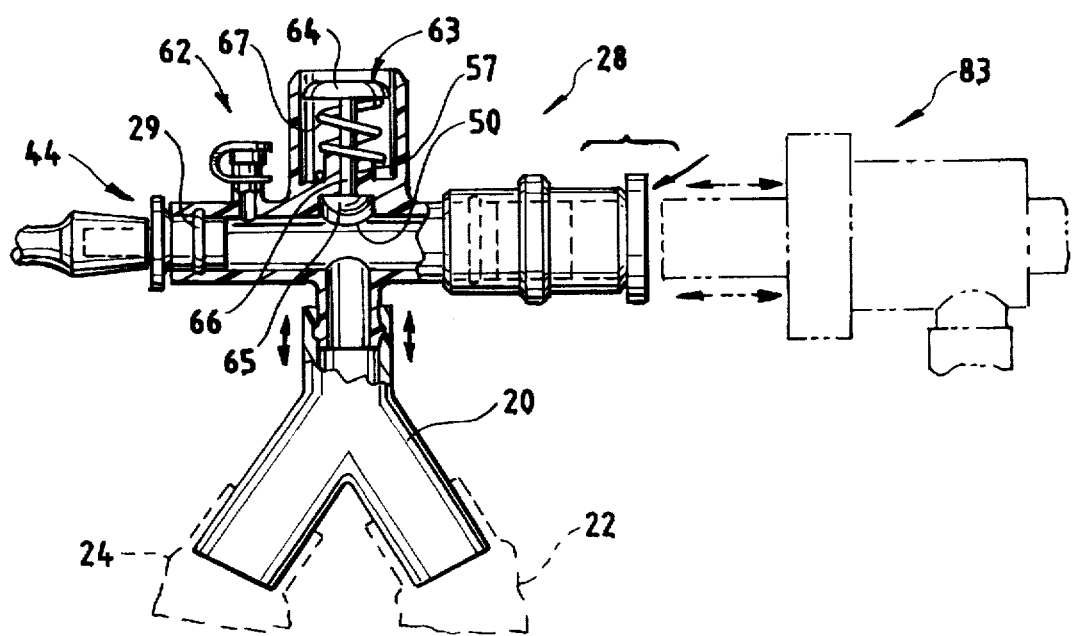
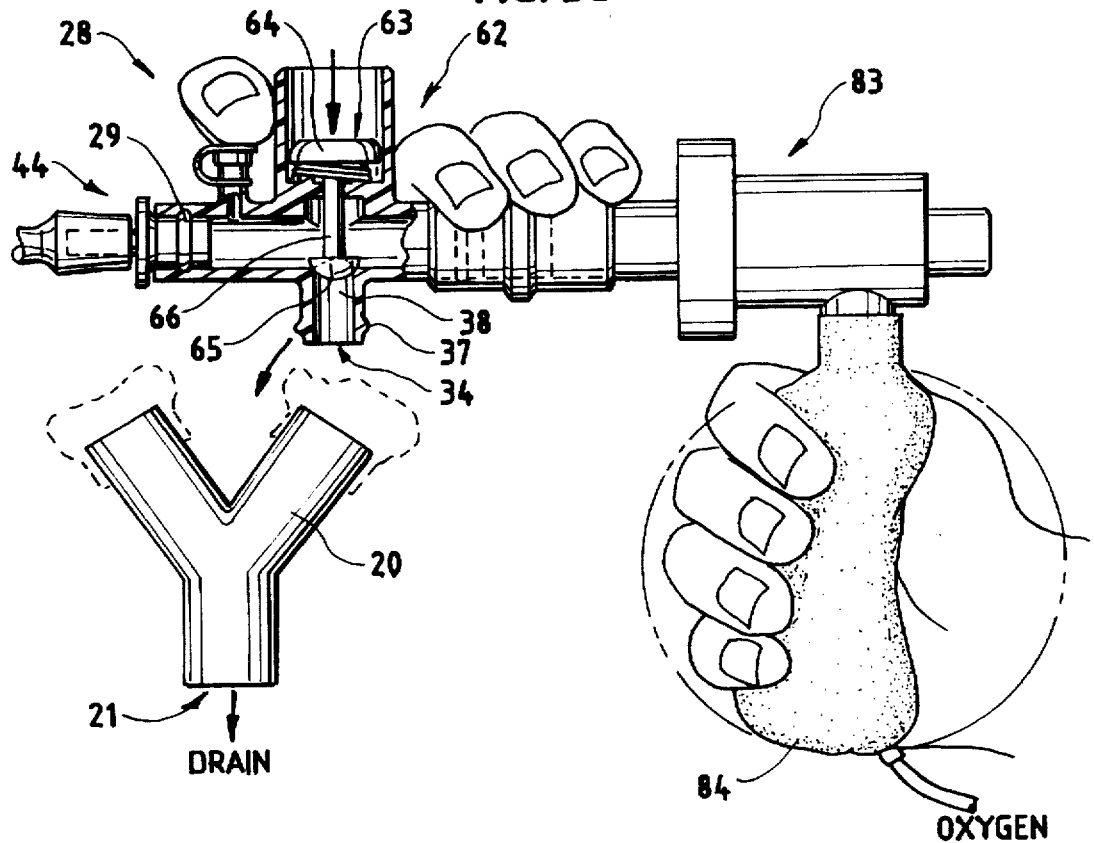

UNIVERSAL RESPIRATORY APPARATUS AND METHOD OF USING SAME

TECHNICAL FIELD

The present invention relates in general to respiratory devices and the method of using them. More particularly, the present invention relates to a universal endotracheal tube adapter and the method of using of adapter to facilitate configuring a closed ventilator system for patient assisted breathing and for obtaining respiratory measurements of a patient without substantial contamination.

BACKGROUND ART

Critical care patients many times require respiratory assistance. In this regard, respiratory systems for patient assisted breathing are common in modem day medical care facilities. Such systems typically include an endotracheal tube insert into the trachea of a patient, a ventilator for supplying air under pressure to the patient and a manifold coupled between the ventilator and endotracheal tube for directing the air under pressure between the ventilator and the endotrachael tube.

While a patient is assisted through such respiratory system, many respiratory procedures and measurements must be undertaken periodically to verify the breathing ability of the patient and to remove fluids accumulated in the trachea and lungs of the patient as well as the ventilator system itself. In order to facilitate such procedures or measurements, medical personnel caring for the patient must necessarily disassemble the respiratory system to temporarily use measurement gauges or suction devices to carry out such measurements and fluid removal procedures. Such procedures then, not only endangered the patient by interrupting the patient assisted breathing but also subjected the patient to unwanted and undesired bacterial infections by opening an otherwise closed ventilation system to potential contamination problems.

Therefore it would be highly desirable to have a new and improved closed ventilator system that is adapted for verifying patient breathing abilities and facilitating the removal of unwanted and undesired trachea and lung fluids without substantially disassembling the system for using measurement gauges and suction catheter devices. Such a system should be convenient to use, relative inexpensive to manufacture, and not require the use of a multiple types and kinds of adapters to effect the necessary measurements and suctioning procedures.

DISCLOSURE OF INVENTION

Therefore, the principal object of the present invention is to provide a new and improved closed ventilator system and method of using it wherein the system is adapted for verifying patient breathing abilities and removing unwanted and undesired trachea and lung fluids from a patient without substantially disassembling the system for using measurement gauges and suction catheter devices.

Briefly, the above and further objects are realized by providing a new and improved closed ventilator system that is readily and conveniently usable with different types of measurement gauges and suction devices without substantial disassembly or opening of the system according to the novel using methods of the present invention.

The new and improved closed ventilator system includes a universal endotracheal tube adapter that is coupled between an endotracheal tube of a patient requiting assisted breathing and a conventional ventilator for supplying air under pressure. The endotrachael tube adapter includes a pair of interconnected hollow body members. One of the hollow body members includes a pair of interconnected air passageways coupled respectively between the ventilator and the endotrachael tube, where the air passageway coupled to the endotrachael tube includes a universal access port for receiving a measurement gauge or a suction catheter device. The other hollow body member is adapted to receive a normally open valve which is disposed substantially opposite the air passageway coupled to the ventilator. The valve is maintained in the open position to permit air under pressure from the ventilator to be supplied to the endotrachael tube. However, when the measurement gauge or suction device is attached to the access port, the valve can be manually operated to close the passageway to the ventilator without closing the other air passageway to facilitate accurate breathing measurements or fluid removal procedures.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIGS. 5A–5B illustrate the steps of draining a ventilator hose system using an Ambag with the endotrachael tube adapter of the closed ventilator system of FIG. 1.

BEST MODE FOR CARRYING OUT THE INVENTION

Figure 1:
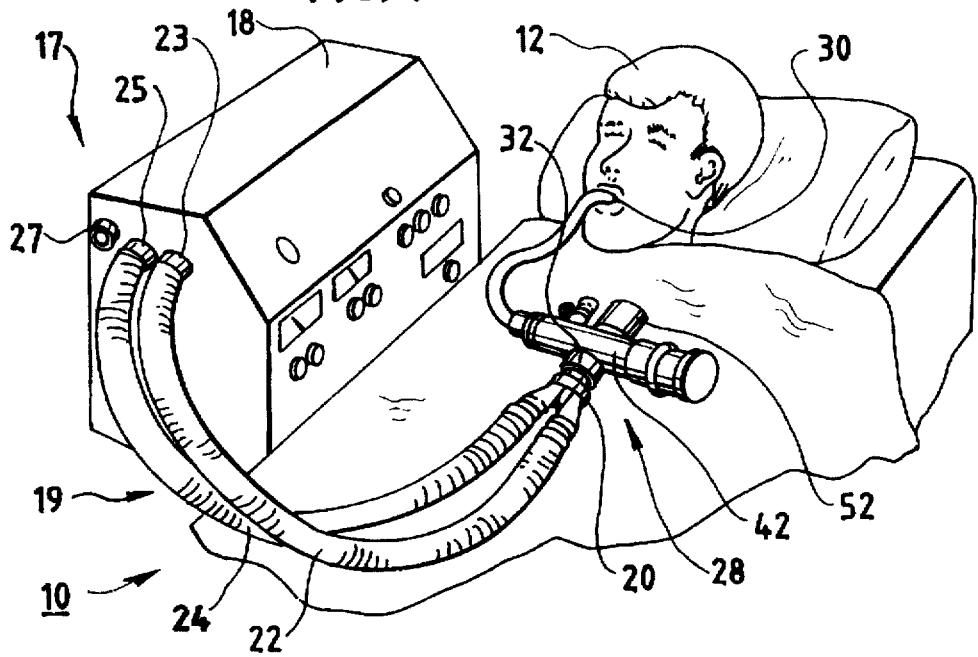
FIG. 1 is a pictorial view of a closed ventilator system which is constructed in accordance with the present invention.

Referring now to the drawings, and more particularly to FIG. 1 thereof, there is illustrated a closed ventilator system 10, which is constructed in accordance with the present invention. The closed ventilator system 10, enables a ventilated patient 12 to receive respiratory treatments, such as the suction removal of accumulated lung cavity fluids without disconnecting the patient from the system 10. The system 10 further facilitates respiratory measurements without disconnecting the patient 12 from the system 10, thus preventing unwanted and undesired system contamination problems.

The closed ventilation system 10, generally comprises an endotrachael tube 30 for insertion into the air passageway of the patient 12, a ventilator arrangement 17 for delivering air under pressure to facilitate patient breathing, and an endotrachael tube adapter 28 coupled between the ventilator arrangement 17 and the endotrachael tube 30 to facilitate respiratory measurements and respiratory medical treatment procedures without disconnecting the patient 12 from either the ventilator arrangement 17 or the endotrachael tube 30.

Considering now the ventilator arrangement 17 in greater detail with reference to FIG. 1, the ventilator arrangement 17 generally includes a ventilator 18 having an inspiratory port 23, an expiratory port 25 and an exhaust port 27. A conventional ventilator hose 19 having an inspiratory limb 22, and expiratory limb 24 is connected to the ventilator 18 via the inspiratory port 23 and the expiratory port 25 respectively to facilitate patient ventilation.

In order to create a single ventilation air passageway between the inspiratory limb 22 and the expiratory limb 24, the closed ventilation system 10 also includes a conventional ventilator hose Y connector 20 having a pair of ventilator ports coupled to the inspiratory and expiratory limbs 22 and 24 respectively. The Y connector 20 also includes an adapter connector 21 with a single output port that is adapted to be received removably rotatably on the endotrachael tube adapter 28. In this regard, the adapter connector 21 is circumscribed with a cutout 26 that is dimensioned to receive therein a protuberance 37 disposed on the exterior surface of the endotrachael tube adapter 28. In this manner a swivel joint 39 is formed between the Y connector 20 and the endotrachael tube adapter 28 enabling relative rotational movement. From the foregoing, those skilled in the art will understand that the endotrachael tube adapter 28 provides an air passageway between the ventilator arrangement 17 and the endotrachael tube 30 to help facilitate machine assisted breathing for the patient 12.

The ventilator 17 is a conventional ventilator, such as a Model 900C Servo manufactured by Seimens, while the ventilator hose system 19 and the associated Y connector 20 as well as the endotrachael tube 30, are all well known to those skilled in the art and will not be described hereinafter in greater detail.

Considering now the endotrachael tube adapter 28 in greater detail with reference to FIG. 1, the endotrachael tube adapter 28 is adapted to be coupled between the ventilator 17 and the endotrachael tube 30 to facilitate respiratory treatments and measurements without contaminating a closed ventilation arrangement such as illustrated in FIG. 1. The endotrachael tube adapter 28 generally includes a lower hollow body member 32 which is adapted to be connected rotatably removably to the ventilator Y connector 20, an intermediate hollow body member 42 which is integrally connected to the lower body member 32 at about a ninety degree angle forming a generally T-shaped configuration, and an upper hollow body member 52 which is integrally connected to the intermediate body member 42 in substantial parallel alignment with the lower body member 32. The intermediate member 42 is further adapted to be connected rotatably removably to the endotrachael tube 30 to facilitate rotation of the endotrachael tube adapter 28 relative to the endotrachael tube 30 without injury to the patient 12.

In order to facilitate respiratory treatments and measurements with out disconnecting the ventilator 17 from the endotrachael tube 30, the endotrachael tube adapter 28 also includes a valve assembly 62 which is disposed within the hollow interior of the upper body member 52.

Figure 2A:
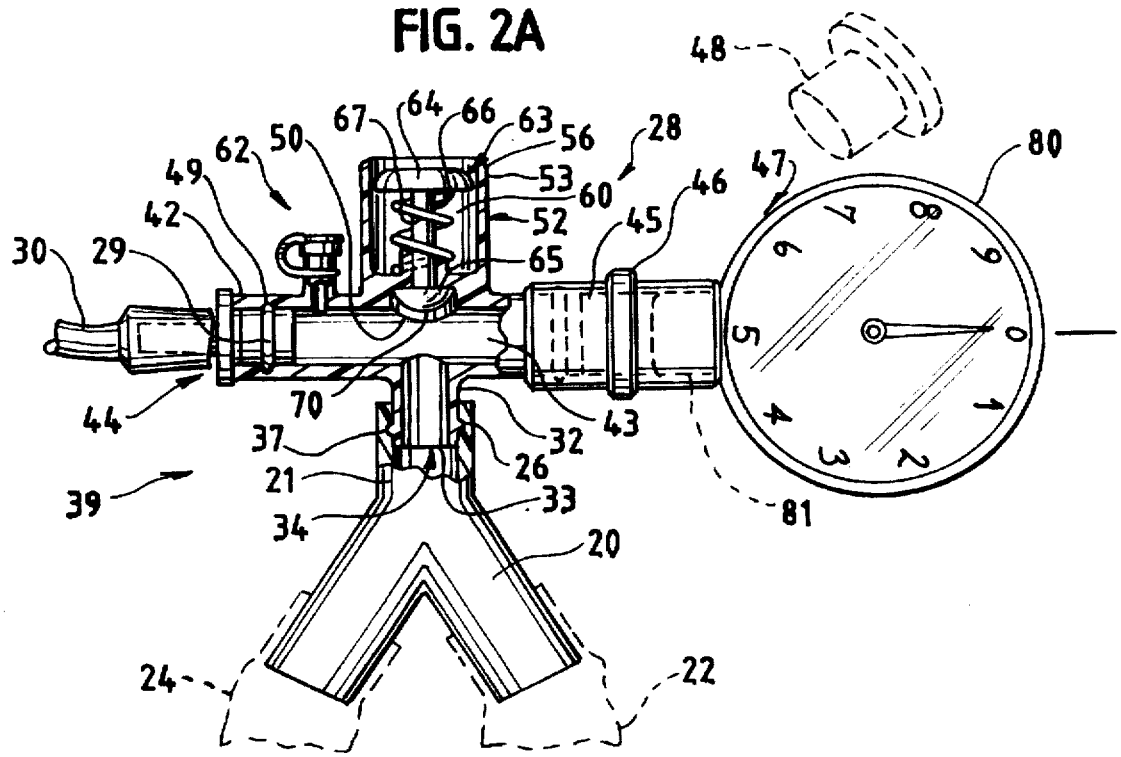
FIGS. 2A–2C illustrate the steps of measuring the expiratory breathing ability of a patient using a expiratory gauge with an endotrachael tube adapter of the closed ventilator system of FIG. 1.
Figure 2B:
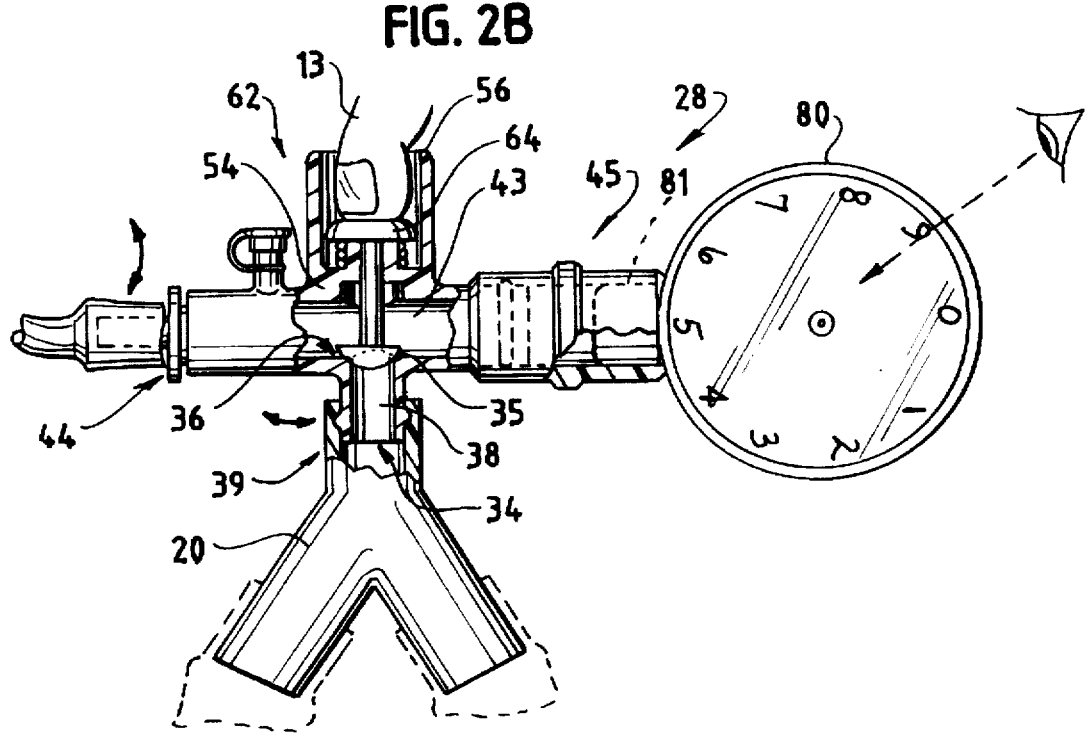

Considering now the lower body member 32 in greater detail with reference to FIGS. 1 and 2, the lower body member 32 is generally tubular in shape having a distal end 33 terminating in a ventilator port 34 and a proximal end 35 terminating in a valve seat port 36. The distal end 33 of the lower body member 32 is circumscribed by the protuberance 37 to enable the cutout 26 within the interior of the Y connector 20 to be received removably rotatably thereon. In this regard, the circumferential protuberance 37 disposed near the distal end 33 of the lower member 32, cooperates with the cutout 26 circumscribing the interior surface of the Y connector 20 near its single output port, permitting the protuberance 37 to be received therein to enable the Y connector 20 and the endotrachael tube adapter 28 to rotate or swivel relative to one another. In this regard, the Y connector rotates about the distal end 34 of the lower body member 32 to enable a respiratory technician (not shown) to rotate the endotrachael tube adapter 28 relative to the Y connector 20 to facilitate attachment of the inspiratory limb 22 and the expiratory limb 24 of the ventilator hose 19 to the ventilator 18, in a fast and convenient manner. This arrangement further facilitate disengagement of the endotrachael tube adapter 28 from the Y connector 20 so that excess water vapor accumulated in the inspiratory and expiratory limbs 22 and 24 respectively can be easily and conveniently drained.

The lower body member 32 is hollow throughout its entire longitudinal length for defining an unobstructed air passageway 38 between the ventilator port 34 and the valve seat port 36. The unobstructed air passageway 38 permits air to pass between the Y connector 20 and the interior of the lower body member 32, and thence, to the hollow interior of the intermediate body member 42 so that air under pressure from the ventilator 18 can be delivered to the patient 12 via the endotrachael tube 30 attached to the intermediate body member 42.

Figure 3A:
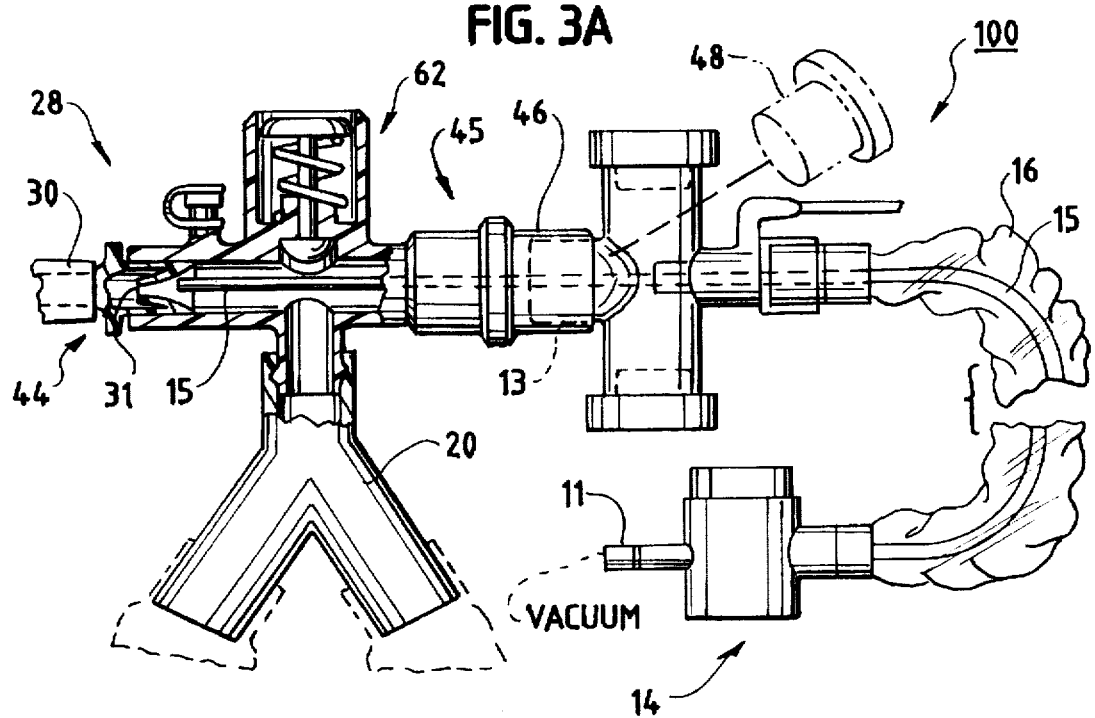
FIGS. 3A–3C illustrate the steps of removing patient lung fluids using a suction catheter with the endotrachael tube adapter of the closed ventilator system of FIG. 1.

Considering now the intermediate hollow body member 42 in greater detail with reference to FIG. 1, the intermediate hollow body member 42 is integrally connected to the lower body member 32 at about the valve seat port 36, and is generally tubular in shape. The intermediate hollow body member 42 extends in diametrically opposite directions from the valve seat port 36 defining a substantially short unobstructed air passageway 43. One end of the air passageway terminates at an endotrachael tube port 44 which is adapted to be coupled to the endotrachael tube 30. The opposite end of the air passageway 43 terminates at a universal or suction port 45 which is adapted to coupled to respiratory equipment such as a suction catheter 14 (FIG. 3) or a respiratory measurement gauge, such as a Wrights gauge 80. A closure cap 46 having an access port 47 with a removal cap member 48, is adapted to be received on the intermediate body member 42 at its opposite end for sealing the suction port 45 when the adapter 28 is not being utilized for respiratory measurement purposes.

As will be explained in greater detail, when the endotrachael tube 30 is coupled to the endotrachael tube adapter 28, the short air passageway 43 of the adapter 28 facilitates the unobstructed passage of a soft flexible catheter tube 15 (FIG. 3A), such as utilized in a Ballard hose suctioning catheter system 14, between the suction port 45 and a small opening 31 centrally disposed in the proximal end of the endotrachael tube 30. In order to enable the endotrachael tube 30 to rotate relative to endotrachael tube adapter 28, to facilitate respiratory treatment and measurements, a circumferential cutout 49 is disposed in the interior of the intermediate body member 42 near the endotrachael tube port 44. A circumferential protuberance 29 disposed on the exterior surface of the endotrachael tube 30 near its proximal end, is captured rotatably in the cutout 49 disposed within the interior of the intermediate body member 42, to facilitate free relative rotation between the adapter 28 and the endotrachael tube 30.

The intermediate body member 42 also includes a valve port 50 which is disposed between the endotrachael tube port 44 and the suction port 46. The valve port 50 is further disposed substantially opposite the valve seat port 36 to form a cross passageway 51 between the lower body member 32 and the upper body member 52. In this regard, the cross passageway 51 extends between the valve seat port 36 of the lower body member 32 and the valve port 50 of the intermediate body member 42. As will be explained hereinafter in greater detail, the cross passageway 51 facilitates the closure of the unobstructed passageway 38 disposed in the lower body member 32.

From the foregoing those skilled in the art will understand that the lower hollow body member 32 and the intermediate hollow body member 42 are integrally connected to form two interconnected air passageways disposed at about ninety degrees to one another for helping to facilitate patient assisted breathing. In this regard, one of the air passageway helps facilitates air pressure measurements to determine the unassisted breathing ability of the patient 12 by providing a short air passageway between the endotrachael tube port and the suction or universal port adapted to receive a breath measurement gauge as will be explained in greater detail. The other air passageway facilitates the delivery of air under pressure to the endotrachael tube port so the patient may be ventilated continuously except for the short period breath measurements are obtained.

Considering now the upper hollow body member 52 in greater detail with reference to FIG. 1, the upper hollow body member 52 generally includes an upstanding circular wall member 53 and a base member 54 having a floor 55. The circular wall member 53 extends upwardly from the floor 55 of the base member 54 terminating in a lip 56 defining a finger receiving access hole 59. An upper valve receiving space or chamber 60 is defined between the floor 55 of the base member 54 and the lip 56 of the upstanding wall member 53. The upper chamber 60 is generally cylindrical in shape and has a sufficient volume for receiving therein for receiving a portion of the valve assembly 62 that facilitates the closure of the unobstructed passageway 38.

The base member 54 includes a lower valve receiving space or chamber 70 that is in coextending alignment with the valve port 50 of the intermediate member 42. The lower chamber 70 is generally cylindrical in shape and is substantially smaller than the upper chamber 60. The lower chamber 70 and the upper chamber 60 are interconnected by a passageway 57. The passageway 57 and the lower chamber 70 are dimensioned for receiving other portions of the valve assembly 62 as will be explained hereinafter in greater detail. The lower chamber 70 is dimensioned to receive substantially the valve member 65 so the valve port 50 is completely blocked by a lower or bottom portion 69 of the valve member 65. In this regard, the bottom portion 69 of the valve member 65 cooperates with the interior wall of the passageway 43 to form a substantially smooth surface for facilitating the passage of respiratory instruments between the endotrachael tube port 44 and the suction port 45.

Considering now the valve assembly 62 in greater detail with reference to FIG. 1, the valve assembly 62 generally includes an actuator 63 having a actuator button or plunger 64 connected to a valve member 65 by a valve stem 66. A biasing spring 67 disposed between the floor 55 of the base member 54 and the underside of the actuator button 64 maintains the valve assembly 62 in a normally open position. The valve member 65 is received sufficiently within the lower chamber 70 when the valve assembly 62 is biased to the open position to substantially prevent interference between the valve member 65 and any respiratory instruments utilized within the passageway 43 for respiratory treatment purposes. Thus for example, a suction catheter tube, such as the catheter tube 15 (FIG. 3A) can pass freely unobstructedly along the passageway 43 between the suction port 45 and the endotrachael tube port 44.

Considering now the operation of the system 10 in greater detail with reference to FIGS. 1-5, the endotrachael tube adapter 28 enables the respiratory technician to accomplish the following respiratory measurements and treatments without disconnecting the patient 12 from the ventilator 17:

1) measure the inspiratory breathing ability of the patient;

2) measure the expiratory breathing ability of the patient; and 3) suction excess trachea or lung cavity fluids from the patient without contamination.

The endotrachael tube adapter 28 also facilitates the following procedures in a fast and convenient manner without contaminating the respiratory system of the patient:

1) drainage of fluids accumulated in the ventilator hose system; and 2) temporary air bag breathing to facilitate ventilator replacement or respiratory measurement procedures.

In operation, the respiratory technician using conventional techniques connects the ventilator 18 to the ventilator hose system 19. In this regard, the inspiratory limb 22 is connected to the inspiratory port 23 of the ventilator 18 while the expiratory limb 24 is connect to the expiratory port 24 of the ventilator 18. Next the ventilator Y connector 20, is attached to the inspiratory limb 22 and the expiratory limb 24 respectively, leaving the output end 21( FIG. 5B) of the ventilator connector 20 free for attachment to the ventilator port 34 of the endotrachael tube adapter 28.

Considering now the method of attaching the endotrachael tube adapter 28 between the ventilator Y connector 20 and the endotrachael tube 30 in greater detail with reference to FIG. 1, the technician inserts the free end 21 of the Y connector 20 onto the distal end 33 of the endotrachael tube adapter 28 a sufficient distance to permit the protuberance 37 thereon to be received within the cutout 26 disposed in the interior wall surface of the Y connector 20. In this manner, the swivel joint 39 is formed so the Y connector 20 can swivel in a three hundred and sixty degree rotation relative to the lower body member 32 of the endotrachael tube adapter 28. Such rotation permits the technician to straighten the inspiratory limb 22 and the expiratory limb 24 of the ventilator hose 19 in a fast and convenient manner should such a corrective maneuver be required.

As will be explained hereinafter, the swivel joint 39 formed between the Y connector and the endotrachael tube adapter 28 also facilitates disconnecting the Y connector 20 from the endotrachael tube adapter 28 in a fast and convenient manner for ventilator hose 19 drainage purposes as illustrated in FIG. 5B.

After connecting the Y connector 20 to the lower body member 32 of the endotrachael tube adapter 28, the technician next inserts the free end of the endotrachael tube 30 a sufficient distance within the endotrachael tube port 44 of the adapter 28 to permit the protuberance 29 on the endotrachael tube 30 to be received in the cutout 49 near the endotrachael tube port 44. In this manner, a swivel joint 41 is formed between the endotrachael tube adapter 28 and the endotrachael tube 30 to help prevent patient injury during the course of the technician performing respiratory measurement and treatment techniques and procedures.

Figure 3B:
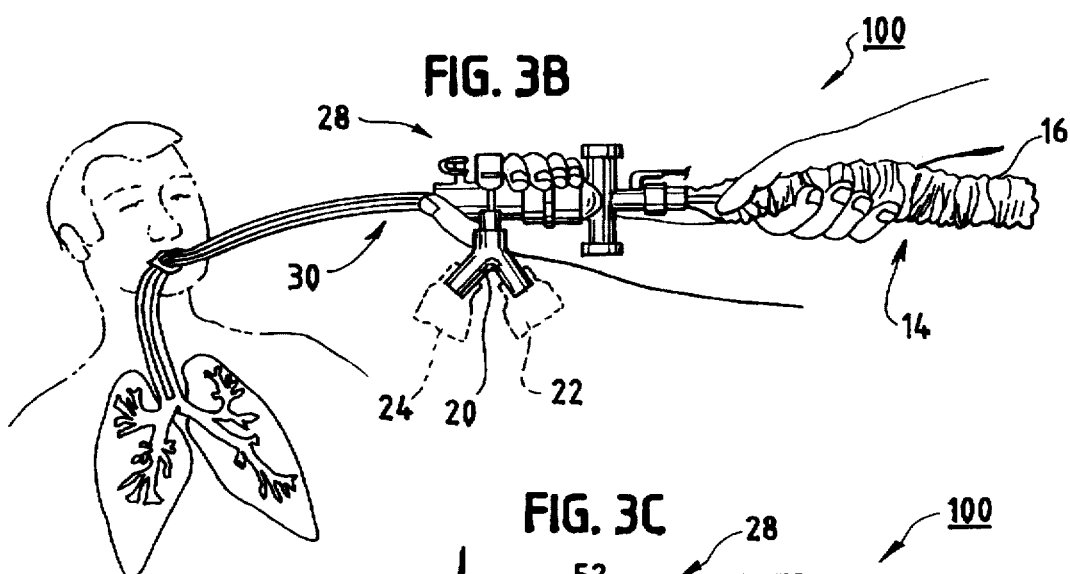
Figure 3C:
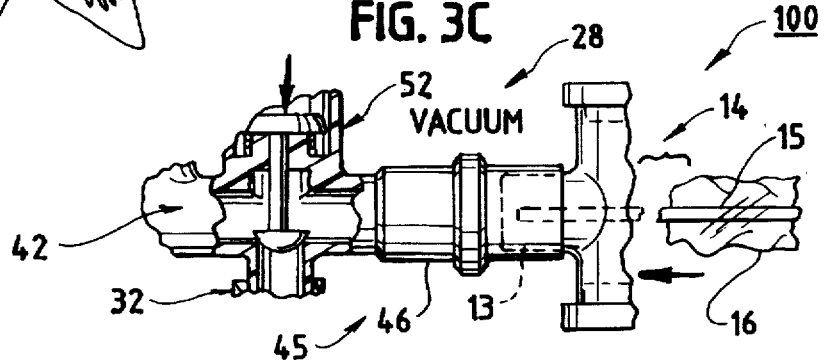

Considering now the method of removing excess fluids from the trachea or lung cavity of the patient 12, in greater detail with reference to FIG. 3, the drainage method generally includes the steps of removing the closure cap 48 opening the suction port 45 of the endotrachael tube adapter 28. Next the free end of the suction catheter system 14 is inserted into the end cap 46 a sufficient distance to secure an distal end body portion 13 of the catheter system 14 at the suction port 45 in a friction tight manner.

Next, as illustrated in FIG. 3B, the catheter tube 15 within the suction catheter system 14 is grasped via an external sleeve member 16 forming part of the catheter system 14 enabling the technician to move the flexible catheter tube 15 forward through the passageway 43, into the small opening 31 of the endotrachael tube 30, and thence, down the endotrachael tube 30 into the lung cavity of the patient 12. Next, a vacuum source outlet 11 is attached to the closed catheter system 14 enabling a vacuum to be established to the lung cavity of the patient for removing fluids from the lung cavity.

Once the excess fluids have been removed from the patient 12, catheter system 14 is disconnected from the vacuum source outlet 11. Once the catheter system 14 has been disconnected from the vacuum source outlet 11, the technician grasps the catheter tube 15 via the external sleeve 16 and slowly withdraws the catheter tube 15 from the endotrachael tube 30 and the endotrachael tube adapter 28 until the distal end of the catheter tube 15 is disposed entirely within the free end 13 of the catheter system 14 for subsequent use. In this manner, the suction catheter system 14 once secured to the closed ventilator system 10, the system is converter to a closed catheter system 100 that may repeatedly utilized with the patient 12 without causing unwanted and undesired system contamination.

Considering now the method of measuring the expiratory breathing ability of the patient 12 in greater detail with reference to FIG. 2, the technician removes the closure cap 48 from the end cap 46 to provide an access to the suction port 45. Next, the technician attaches a spirometer 80, such as the Wright spirometer 80, into the end cap 46 disposed on the intermediate body member 42 at its open suction port 45 end. In this regard, the spirometer 80 includes an input port adapter 81 that is received removably into the end cap 46 in a friction tight fit. Thus, the volume of the air exhaled from the patient 12 can be measured in a convenient and highly accurate manner.

As best seen in FIG. 2A, once the spirometer 80 has been coupled to the endotrachael tube adapter 28, the technician begins to observe the breathing rhythm of the patient 12 to determine the inspiratory and expiratory breathing periods. In this regard, after the inspiratory and expiratory periods have been determined, the technician grasps the adapter 28 and slowly rotates the adapter 28 relative to the endotrachael tube 30 to position the adapter 28 in a convenient location so a digit D of the technician can be received within the finger access hole 59 to engage and depress the actuator button 64 downwardly while the adapter 28 is held in a stationary position relative to the endotrachael tube 30. When the adapter 28 has been so positioned, the technician depresses the actuator button 64 a sufficient distance downwardly to cause the valve member 65 to be received sealing into the valve seat port 36 causing the lower air passageway 38 to be blocked temporarily. In this manner, the air under pressure delivered by the ventilator 18 is blocked from reaching the patient 12. Thus, when the technician depresses the actuator button 64 at the end of the patient inspiratory or inhale cycle, the patient 12 will exhale into the unobstructed air passageway 43 allowing the tidal volume of the air exhaled from the patient 12 to pass directly into the spirometer 80 attached to the suction port 45. The technician is then able to read the metric liter volume of the exhaled air.

At the end of the exhale cycle, the technician releases the actuator button 64 allowing the air under pressure to once again to be delivered to the endotrachael tube 30 via the adapter 28. The technician, if desired, may at the end of another inhale cycle, depress the actuator button 64 to take a confirmation measurement.

Figure 2C:
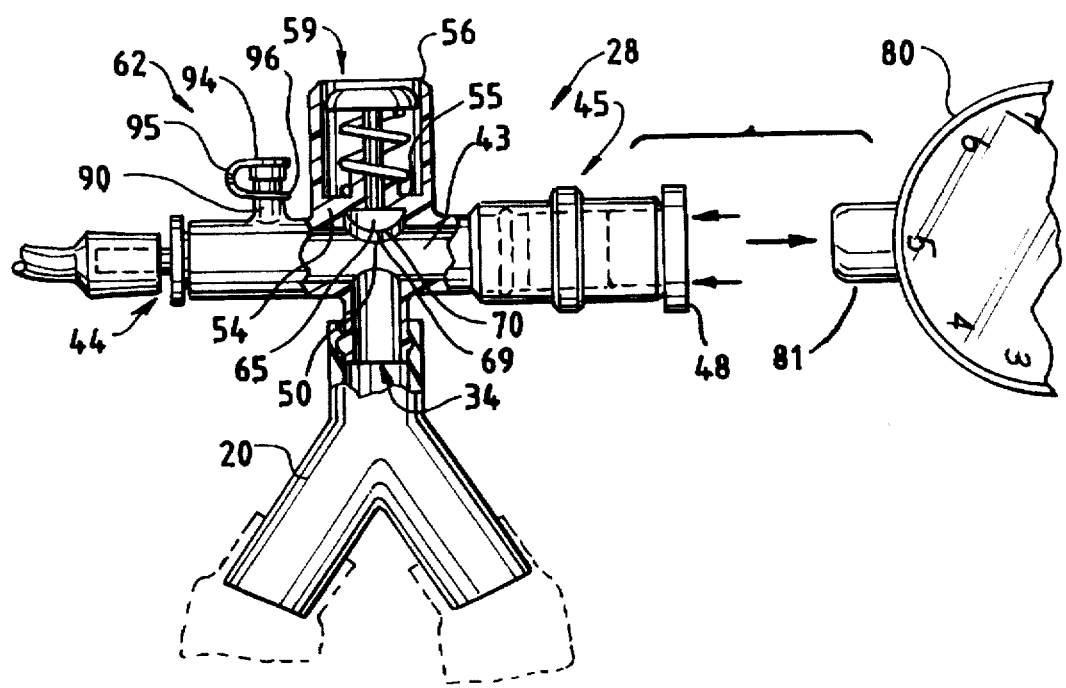

Once the technician is satisfied that he or she has obtained an accurate measurement of the tidal volume of air exhaled by the patient 12, the spirometer 80 may be removed from the endotrachael tube adapter 28. As best seen in FIG. 2C, the technician then replaces the closure cap 48 to once again close the ventilation system 10.

From the foregoing, those skilled in the art will appreciate that method of measuring the tidal volume of air exhaled by the patient 12 via a short air passageway defined by the passageway of the endotrachael tube 30 and the short unobstructed air passageway 43 of the intermediate hollow body member 42, provides a substantially more reliable measurements then those obtained by attaching the spirometer to the exhaust port 27 of the ventilator 18 so the tidal volume can be measured through the long air passageway defined by the passageway of the endotrachael tube 30, the ventilator hose 19, the Y connector 20 and the ventilator 18 to its associated exhaust port 27. In addition, since the spirometer 80 is attached to the adapter 28 in an air tight fit, that enable the volume readings to be more reliable than attempting to engage the input port 81 of the spirometer 80 with the exhaust port 27 of the ventilator 18.

Considering now the endotrachael tube adapter 28 in still greater detail with reference to FIG. 1, in order for inspiratory air measurements to be taken at or near the small opening 31 at the proximal end of the endotrachael tube 30, the intermediate body member 42 includes a hollow upstanding or vertical member 90 integrally connected to the unobstructed air passageway 43 between the endotrachael tube port 44 and the valve port 50 of the endotrachael tube adapter 28. The upstanding member 90 is generally tubular in shape and includes at one of its ends a gauge port 91 and at its other end, an inlet port 92 for defining an auxiliary air passageway 93 therebetween. The inlet port 92 is spaced apart from the cutout 49 a sufficient distance to prevent the proximal end of the endotrachael tube 30 from blocking the auxiliary air passageway 93 when the endotrachael tube 30 is coupled to the adapter 28. A gauge port cap 94 having a securing strap 95 with a hole 96 is received on the vertical tube member 90 for sealing the auxiliary air passageway 93 when the gauge port 91 is not in use for respiratory measurement purposes.

Figure 4A:
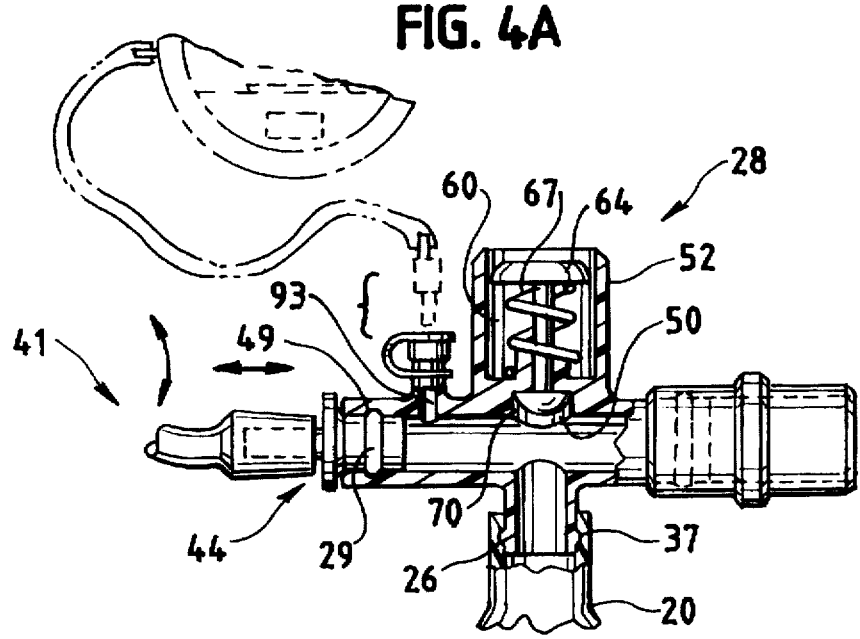
FIGS. 4A–4B illustrate the steps of measuring the inspiratory breathing ability of a patient using a Magnehelic gauge with the endotrachael tube adapter of the closed ventilator system of FIG. 1.
Figure 4B:
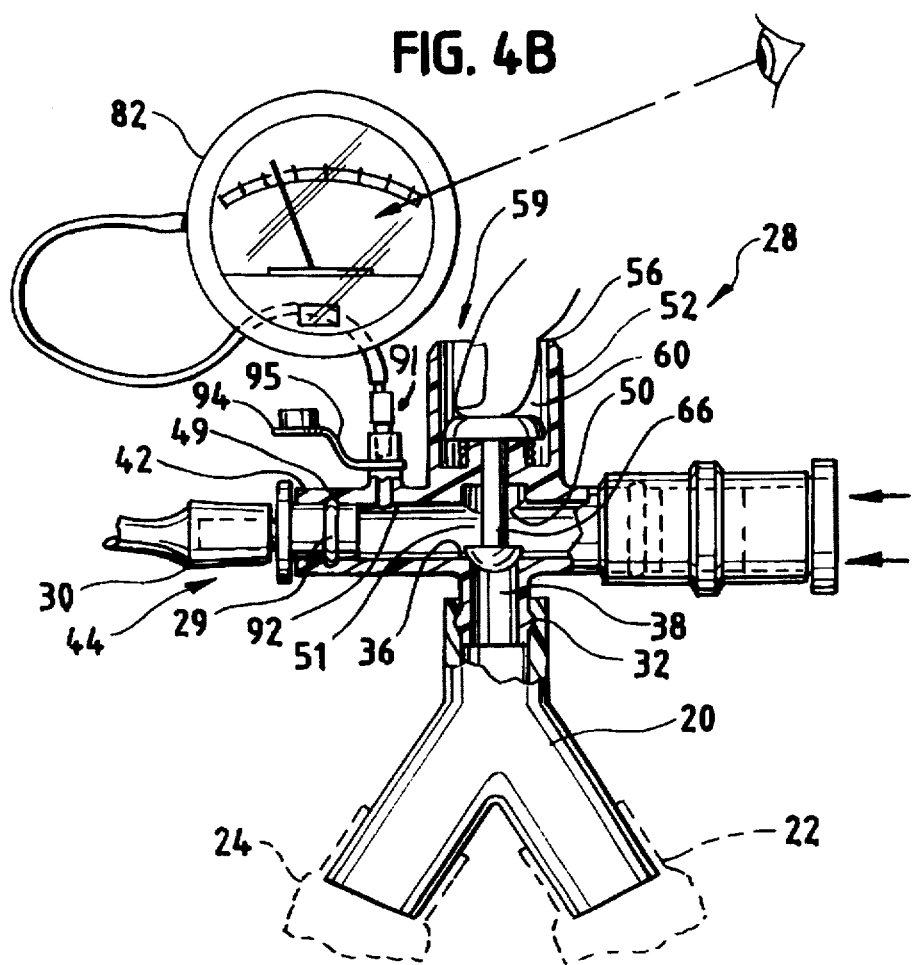

Considering now the upper member 52 in still greater detail with reference to FIG. 5, the upper member 52 further includes an upstanding retaining wall member or stop 73. The stop 73 is centrally disposed on the floor 55 for helping to retain the spring 67 within the upper chamber 60. The retaining wall member is generally tubular in shape and helps prevent excess pressure from being applied to the valve stem 66 when the actuator button 64 is fully depressed. In this regard, as best seen in FIGS. 4A and 4B, when the technician depresses the actuator button 64, the spring 67 assumes a fully compressed configuration about the retaining wall 73. The underside of the actuator button 64 comes into resting engagement with a top or lip portion 74 of the retaining wall 73 preventing further downward travel by the actuator 63. The lip 74 defines an opening to the valve stem passageway 57 extending between the upper chamber 60 and the lower chamber 70. A resilient sealing ring 68 is secured at the lip 74 engaging the valve stem 66 for maintaining a substantially air tight seal between the upper chamber 60 and the lower chamber 70.

From the foregoing those skilled in the art will understand that the upper hollow body member 52 includes two interconnected chambers 60, 70 which are disposed in substantial parallel alignment with the ventilator port for further helping to facilitate air pressure measurements so the breathing ability of a ventilated patient may be obtained without disconnecting the patient 12 from the ventilator system 17. In this regard, the normally open valve assembly is mounted partially within the upper and lower chamber 60 and 70 for permitting the technician to temporarily interrupt the delivery of air under pressure to the endotrachael tube port without interrupting the fluid communication between the endotrachael tube port and the universal or suction port. Thus, air pressure measurement to determine the unassisted breathing ability of the patient 12 can be obtained from the universal port without the patient receiving air under pressure.

Considering now the method of measuring the inspiratory breathing ability of the patient 12 in greater detail with reference to FIG. 4, the technician removes the gauge port cap 94 from the gauge port 91 of the vertical member 90 and attaches to the vertical member 90 at the open gauge port 91 a Magnehelic gauge 82 in order to measure the volume of air inhaled into the lungs of the patient 12. After the technician connects the Magnehelic gauge 82 to the port 91, the technician maintains the endotrachael tube 30 in a stationary position and rotates the adapter 28 relative to the endotrachael tube 30 a sufficient distance to facilitate the reading of the Magnehelic gauge 82. The technician then observes the inspiratory and expiratory breathing cycles in order to determine the proper time period for closing the valve assembly 62. Once the breathing cycles have been determined, the technician depresses the actuator button 64 as best seen in FIG. 4B to close the air passageway 38 at the beginning of the inspiratory cycle, thus preventing the air under pressure from reaching the endotrachael tube 30. The patient 12 in response to the lack of air, breaths naturally causing a negative pressure through the Magnehelic gauge 82 via the endotrachael tube 30 and the upstanding vertical member 90. At the end of the inspiratory cycle the technician releases the button 64 again opening the air passageway 38 so the air under pressure is once again directed to the endotrachael tube to facilitate patient breathing. After releasing the button 64, the technician holds the adapter 28 in a stationary position while he or she removes the Magnahelic gauge 82 from the adapter 28 and closes the gauge port 91 utilizing the gauge port cap 94 to seal the gauge port 91.

In a similar manner, should the technician need to determine the expiratory breathing capabilities of the patient, the above mentioned Magnahelic gauge procedure can be repeated during the inspiratory cycle causing a positive pressure reading on the magnehlic gauge 82.

Considering now the method of supplying air to the patient 12 should the ventilator 18 fail or otherwise need replacement in greater detail with reference to FIG. 5, the technician removes the suction port closure cap 48 and attaches a manual oxygen system, such as an Ambag system 83 to the adapter 28 via the end cap 46. In this regard, the Ambag system 83 includes an air bag 84, and supply of oxygen that can be utilized while the ventilator 18 is replaced. In operation, when the manual system 83 is attached to the adapter 28, the technician depresses the actuator button 64 with the finger of one hand and removes the Y connector 20 with the other hand. When the Y connector 20 is removed, the technician can continue to manually manipulate the air bag 84 in a rhythmic manner supplying air to the patient 12 until such time as a replacement ventilator (not shown) is attached to the adapter 28. In this regard, the technician insert the Y connector 20 of the replacement ventilator onto the lower body member 32 at the ventilator port 34. Once the new ventilator is attached to the adapter 28, the technician releases the actuator button 64 providing air under pressure to the endotrachael tube 30. The technician completes the procedure by removing the manual system 83 from the end cap 46 and then seals the suction port 45 with the closure cap 48.

From the foregoing, it will be understood by those skilled in the art, that the utilization of the endotrachael tube adapter 28 in combination with the endotrachael tube 30 facilitates both machine aided breathing via the ventilator arrangement 17 or manually aided breathing via the manual system 83. Those skilled in the art will further understand that depressing the actuator 63 while removing the Y connector 20 from the adapter 28 enables the technician to invert the ventilator hose 19 and Y connector 20 for drainage purposes as illustrated in FIG. 5B, without the spraying of any accumulated water or bodily fluids.

Although the above describe system and procedures were described using an endotrachael tube with the adapter 28, those skilled in the art will understand that a tracheal bode arrangement can also be utilized.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. An endotrachael tube adapter to facilitate respiratory measurements of a ventilated patient, comprising:

a hollow body member having a lower body portion and an upper body portion, said lower body portion having two interconnected air passageways disposed at about ninety degrees to one another for helping to facilitate patient assisted breathing;

one of the air passageways having an endotrachael tube port at one of its ends and a universal port at the other one of its ends for helping to facilitate air pressure measurements to determine an unassisted breathing ability of a ventilated patient;

the other one of the passageway having a ventilator port at one of its ends and being interconnected at its other end at about between said endotrachael tube port and said universal port for facilitating delivery of air under pressure to said endotrachael tube port to permit a patient to be ventilated therefrom;

said upper body portion having two interconnected chambers disposed in substantial co-alignment with said ventilator port for further helping to facilitate air pressure measurements to determine an unassisted breathing ability of a ventilated patient;

valve means mounted within said chambers for permitting a technician to temporarily interrupt the delivery of the air under pressure to said endotrachael tube port without interrupting fluid communication between said endotrachael tube port and said universal port so that air pressure measurements to determine an unassisted breathing ability of a ventilated patient can be obtained from the universal port without a patient receiving air under pressure via the ventilator port.

2. An endotrachael tube adapter according to claim 1, further comprising:
   end cap means mounted on said lower body portion at about said universal port for sealing it to help facilitate the delivery of air under pressure from said ventilator port to said endotrachael tube port.

3. An endotrachael tube adapter according to claim 2, wherein said end caps means includes a removal closure cap for providing an access opening to said universal port;
   said access opening being dimensioned for receiving therein in an air tight fit a breath measurement gauge for determining an unassisted breathing ability of a ventilated patient.

4. An endotrachael tube adapter according to claim 3, wherein said chambers include a large upper chamber and a small lower chamber;
   said upper chamber being sufficiently large for receiving therein an actuator portion of said valve means; and
   said lower chamber being sufficiently small for receiving therein a valve stop portion of said valve means;
   said valve stop portion being in disposed opposite said ventilator port for temporarily interrupting the flow of the air under pressure to said endotrachael tube port when said valve means is actuated to a closed position.

5. An endotrachael tube adapter according to claim 1, wherein said valve means is spring biased valve means.

6. An endotrachael tube adapter according to claim 5, wherein said spring biased valve means includes:
   finger engageable actuator means mounted within said upper chamber;
   valve stop means mounted within said lower chamber; and
   valve stem means coupled between said finger engageable actuator means and said valve stop means for enabling the downward movement of said actuator means to move said valve stop means in a rectilinear path of travel a sufficient distance for temporarily preventing the air under pressure delivered via said ventilator port from being delivered to said endotrachael tube port without interrupting the fluid communication between said endotrachael tube port and said universal port.

7. An endotrachael tube adapter according to claim 6, wherein said finger engageable actuator means includes:
   a finger engageable actuator button connected to said valve stem means at one of its ends;
   a spring for supporting from below said finger engageable actuator button within said upper chamber and for holding said valve means in a normally open position;
   spring retaining means mounted on a floor portion of said upper chamber for securing said spring between the floor portion of the upper chamber and said finger engageable actuator button.

8. An endotracheal tube adapter according to claim 1, wherein said upper body portion includes:
   a base member;
   a tall upstanding wall member integrally connected to said base member at about its peripheral boundaries for defining said upper chamber; and
   a short upstanding wall member integrally connected to said base member and spaced inwardly from said upstanding wall member for defining an actuator stop.

9. An endotrachael tube adapter according to claim 1, wherein said lower body portion includes at about said ventilator port, a Y connector retaining means for facilitating securing removably rotatably a ventilator hose Y connector.

10. An endotrachael tube adapter according to claim 9, wherein said Y connector retaining means is a protuberance circumscribing an exterior surface portion of the air passageway adjacent to said ventilator port.

11. An endotrachael tube adapter according to claim 1, wherein said lower body portion further includes:
   a gauge port disposed between said endotrachael tube port and said universal port for facilitating respiratory measurements;
   a gauge port end cap for sealing said gauge port when it is not in use to facilitate respiratory measurements;
   a cutout circumscribing an interior surface portion of said air passageway at about said endotrachael tube port for facilitating securing removably rotatably the endotrachael tube to the endotrachael tube adapter; and
   a protuberance circumscribing an exterior surface portion of said air passageway at about said ventilator port for facilitating securing removably rotatably a ventilator hose Y connector to the endotrachael tube adapter.

12. An endotrachael tube adapter according to claim 1, wherein said chambers include an upper chamber and a lower chamber, said upper chamber being substantially larger in volume than said lower chamber for receiving therein an actuator portion of said normally open valve means; and
   said actuator portion of said valve means including an elongated valve stem extending between said upper and lower chambers, a finger engageable actuator button connected to one terminal end of said valve stem, said actuator button being recessed within said upper chamber a sufficient distance for preventing accidental actuation, and a valve head connected to the other terminal end of said valve stem, said valve being disposed substantially completely within said lower chamber without obstructing the fluid communication path between said endotrachael tube port and said universal port.

13. An endotrachael tube adapter according to claim 12, wherein the air passageway including said ventilator port includes a valve seat port, said valve seat port being dimensioned for receiving sealing therein said valve head to substantially prevent the air under pressure from passing to the air passageway including said endotrachael tube port.

14. An endotrachael tube adapter according to claim 1, wherein said lower body portion further includes a gauge port disposed between said endotrachael tube port and said universal port for facilitating respiratory measurements; and
   gauge port cap means for sealing said gauge port when it is not in use to facilitate respiratory measurements.

15. An endotrachael tube adapter according to claim 14, wherein said gauge port cap means including a cap and a retaining strap for securing said cap to said lower body portion.

* * * * *